(12) United States Patent
Kremeier

(10) Patent No.: US 11,446,456 B2
(45) Date of Patent: Sep. 20, 2022

(54) DEVICE FOR RECORDING AND GRAPHIC REPRESENTATION OF PRESSURE-VOLUME CURVES

(71) Applicant: Loewenstein Medical Technology S.A., Luxembourg (LU)

(72) Inventor: Peter Kremeier, Karlsruhe (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 572 days.

(21) Appl. No.: 16/295,042

(22) Filed: Mar. 7, 2019

(65) Prior Publication Data

US 2019/0275276 A1 Sep. 12, 2019

(30) Foreign Application Priority Data

Mar. 9, 2018 (DE) .......................... 102018001909.9

(51) Int. Cl.
*A61M 16/00* (2006.01)
*A61B 5/08* (2006.01)
*A61B 5/00* (2006.01)

(52) U.S. Cl.
CPC .......... *A61M 16/024* (2017.08); *A61B 5/0803* (2013.01); *A61B 5/0816* (2013.01); *A61B 5/743* (2013.01); *A61M 16/0003* (2014.02); *A61M 2016/003* (2013.01); *A61M 2016/0027* (2013.01); *A61M 2205/502* (2013.01)

(58) Field of Classification Search
CPC ...... A61B 5/0803; A61B 5/0816; A61B 5/743
See application file for complete search history.

(56) References Cited

U.S. PATENT DOCUMENTS 5,876,352 A * 3/1999 Weismann ........ A61M 16/0051
600/529

* cited by examiner

*Primary Examiner* — Steven O Douglas
(74) *Attorney, Agent, or Firm* — Abel Schillinger, LLP

(57) ABSTRACT

A device for recording and displaying a pressure-volume curve, in which a gas stream is generated by a gas source under control of a control unit and conveyed via a hose to a patient, wherein a flow sensor determines the gas stream and the control unit computes and records the administered gas volume and wherein a pressure sensor determines the gas pressure and the control unit records the pressure and determines a pressure slope and determines a pressure-volume curve from the pressure and the volume and displays it on a display screen or stores it for a display.

20 Claims, 5 Drawing Sheets

DEVICE FOR RECORDING AND GRAPHIC REPRESENTATION OF PRESSURE-VOLUME CURVES

CROSS-REFERENCE TO RELATED APPLICATIONS

The present application claims priority under 35 U.S.C. § 119 of German Patent Application No. 10 2018 001 909.9, filed Mar. 9, 2018, the entire disclosure of which is expressly incorporated by reference herein.

BACKGROUND OF THE INVENTION

1. Field of the Invention

The present invention relates to a device for recording and displaying pressure-volume curves.

2. Discussion of Background Information

The recording of a pressure-volume curve (P/V curve) is a routine method for describing the respiratory-mechanical conditions of the respiratory tract. PV curves can typically be divided into three segments, which are separated from one another by two inflection points. There is usually a first segment having low compliance. This is adjoined by a middle, linear segment having greater compliance (CLIN). These two segments are separated by the lower inflection point (LIP). The middle steep component is ended by the upper inflection point (UIP), following which the curve becomes flatter again.

The accuracy of the measured values is presently poor and the recording of a pressure-volume curve requires a large amount of expert knowledge.

It would therefore be desirable to simplify and improve the recording of pressure-volume curves.

SUMMARY OF THE INVENTION

The invention provides a device for recording and displaying a pressure-volume curve, in which a gas stream (flow or volume) is generated by a gas source under control of a control unit and conveyed via a hose to or from a patient, wherein a flow sensor determines the gas flow and the control unit computes and records the gas volume or the flow and wherein a pressure sensor determines the gas pressure and the control unit records the pressure and determines a pressure slope and determines a pressure-volume curve from the pressure and the volume or flow and displays it on a display screen or stores it for a display. The control unit computes the pressure-volume curve for the inspiration and/or expiration in consideration of the gas stream and the pressure slope and computes and displays steep components or straight lines of the pressure-volume curve.

According to the invention, the gas stream can correspond to an inspiration (or inflation) and/or an expiration (or deflation). The pressure slope can be positive or negative.

Gas stream and gas volume and pressure and flow can be positive or negative.

The hose can be a double-lumen or multi-lumen hose or a simple hose.

The gas source can comprise a controllable fan and/or valves and/or a pressurized gas source.

The invention furthermore provides a device for recording and displaying a pressure-volume curve, in which a gas stream is generated by a gas source under control of a control unit and conveyed via a hose to a patient, wherein a flow sensor determines the gas stream and the control unit computes and records the administered gas volume and wherein a pressure sensor determines the gas pressure and the control unit records the pressure and determines a pressure slope and determines a pressure-volume curve from the pressure and the volume and displays it on a display screen or stores it for a display. The control unit computes the inspiratory compliance as a quotient of the gas stream and the pressure slope, wherein the inspiratory compliance is displayed on the display screen and wherein the control unit computes an LIP (lower inflection point, 21) and a UIP (upper inflection point, 20), and uses the LIP and the UIP in the pressure-volume curve for the display of a straight line, which is defined or delimited by the LIP and the UIP.

According to the invention, the display screen can be a component of the device (of the respirator) or it can be an external display screen, which at least temporarily communicates with the device.

The device may also be characterized in that the control unit generates a uniform, continuous gas stream (3).

The device may also be characterized in that the control unit generates a discontinuous gas stream (3).

The device may also be characterized in that the control unit (2) computes an LIP (lower inflection point) and/or a UIP (upper inflection point) as 67% of the maximum inspiratory compliance (14).

The device may also be characterized in that the straight line through LIP and UIP on the display screen (9) is displaceable or changeable by user selection.

The device may also be characterized in that if LIP and/or UIP are not determinable, a replacement straight line (12) having the slope of the maximum inspiratory compliance (14) is displayed.

The device may also be characterized in that the value of the LIP and/or UIP is numerically displayed on the display screen (8).

The device may also be characterized in that the control unit (2) carries out the computation of the pressure slope by means of linear regression over at least 200, preferably 500, measurement points.

The device may also be characterized in that the computation only begins 200, preferably only 500, ms after the start of the inspiration.

The device may also be characterized in that the control unit (2) computes the gas volume (5) as the summation of the volume stream components.

The device may also be characterized in that the recording of the pressure-volume curve (8) is started by user selection.

The device may also be characterized in that the control unit executes an automatic analysis of the pressure-volume curve (8) to determine at least one parameter and at least temporarily takes this parameter into consideration for the control of the gas source (1) by the control unit (2).

The device may also be characterized in that the control unit executes an automatic analysis of the pressure-volume curve (8) to determine at least one parameter, and computes a setting value for the control unit (2) for this parameter for the control of the gas source and displays it on the display screen (9).

The device is alternatively or additionally also used according to the invention for recording and displaying a pressure-volume curve in which a gas stream (3) is generated by a gas source (1) under control of a control unit (2) and conveyed via a hose (13) to or from a patient, wherein a flow sensor (4) determines the gas stream (3) and the control unit (2) computes and records the gas volume (5), and wherein a pressure sensor (6) determines the gas pressure (7) and the control unit (2) records the pressure and determines a pressure slope (17) and determines a pressure-volume curve (8) from the pressure (7) and the volume (5) and displays it on a display screen (9) or stores it for a display. The control unit (2) uses the breath volume VT (37) from the present or the prior respiration to compute a pressure-volume curve j (38) and determines the pressures Pawj (34) and/or Pawj80 (35) using the value of j (38).

The device may also be characterized in that the control unit uses the breath volume VT (37) from the present or the prior respiration to compute a pressure-volume curve j (38).

The device may also be characterized in that the control unit determines the pressures Pawj (34) and/or Pawj80 (35) using the value of j (38).

The device may also be characterized in that the Pawj80 (35) is a percentage value (the 80% value) of the pressure Pawj.

The device may also be characterized in that the control unit connects the PEEP (23) and Pawj (34) by means of a straight line (41) as Cdyn and displays it on the display screen.

The device may also be characterized in that the control unit connects 0.8 Pawj (35) and Pawj (34) by means of a straight line (42) as C20 and displays it on the display screen.

The device may also be characterized in that the control unit determines the pressure slope (36) in the range between 0.8 Pawj (35) and Pawj (34) (preferably by means of linear regression) and displays a corresponding straight line on the display screen.

The device may also be characterized in that the control unit computes a stress index (36) and displays it or stores it from the pressure slope (36) between 0.8 Pawj (35) and Pawj (34).

The device is alternatively or additionally also used according to the invention for recording and displaying a pressure-volume curve, in which a gas stream (3) is generated by a gas source (1) under control of a control unit (2) and conveyed via a hose (13) to or from a patient, wherein a flow sensor (4) determines the gas stream (3) and the control unit (2) computes and records the gas volume (5), and wherein a pressure sensor (6) determines the gas pressure (7) and the control unit (2) records the pressure and determines a pressure slope (17) and determines a pressure-volume curve (8) from the pressure (7) and the volume (5) and displays it on a display screen (9) or stores it for a display. The control unit (2) records a pressure-volume curve (31) for the expiration or determines it, wherein the pressure slope (17) is a negative pressure slope and gas stream and/or volume can also be negative.

The device may also be characterized in that the control unit determines the pressure-volume curve (31) from the quotient of the mean flow and the specified pressure ramp.

The device may also be characterized in that the control unit determines the points P(Cmax) (33) and PMC (32) from the pressure-volume curve (31), wherein PMC (32) is a component or fraction of P(Cmax) (33), for example at 0.67 Cmax.

The device may also be characterized in that the control unit effectuates a numeric display of PMC (32) and/or a graphic display of C(p) and V(p) with overlay of displaceable lines on the display screen.

The device may also be characterized in that the control unit displays the pressure-volume curve (31) for the expiration on the display screen and displays a straight line which intersects the points P(Cmax) (33) and PMC (32).

Subject matter of the invention is also the automatic determination of the inflection points of a pressure-volume curve.

Subject matter of the invention is also the automatic derivation of important characteristic variables, which are relevant for respiration, from a pressure-volume curve.

Subject matter of the invention is also a respiratory-mechanical maneuver which displays a quasi-static P/V curve (pressure/volume) both in the inspiration leg and also in the expiration leg. During the maneuver, the airway pressure is slowly increased to a maximum level (Pmax) in the inspiration by a uniform flow and then slowly reduced to a minimum level (Pstart) by an adapted pressure setting (linear speed analog to set flow).

The total time of the maneuver is calculated and displayed at the beginning.

The overlay of lines enables the graphic analysis of the curve, including identification of the inflection points.

At the same time, the differential compliance and the respective ratio between PAW and compliance (separate inflation/deflation) are displayed in tabular form, and also C20/C stress index as values.

PV curves have a linear to sigmoid profile. The expiratory tidal volume is typically plotted on the abscissa and the transpulmonary pressure is plotted on the ordinate. The LIP is the first point of the PV curve having maximum curvature. Up to this point, the pressure per volume step increases particularly strongly. The LIP is then the point at which the lung opening pressure is exceeded and after reaching it, the curve rises linearly. The LIP can be overcome by setting the PEEP.

The UIP is accordingly the second point having maximum curvature of the curve. At the UIP, the limit of the lung distensibility is reached, so that following this the pressure slope per volume unit becomes greater again.

The compliance of the lung is a measure of its elastic distensibility and corresponds to the slope of the linear component of the curve (CLIN); it is thus defined as the volume change per pressure change.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
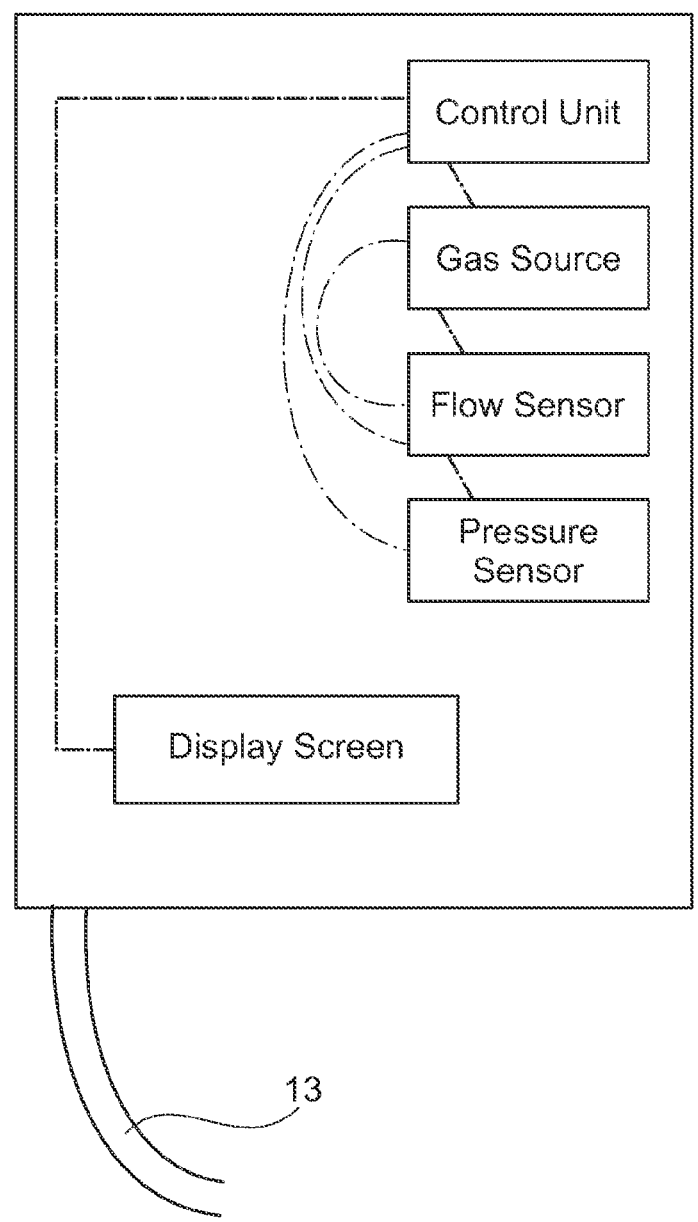
FIG. 1 shows a device according to the invention for recording and displaying a pressure-volume curve.

FIG. 1 shows a device for recording and displaying a pressure-volume curve (8), in which a gas stream (3) is generated by a gas source (1) under control of a control unit (2) and conveyed via a hose (13) to a patient, wherein a flow sensor (4) determines the gas stream (3) and the control unit (2) computes and records the administered gas volume (5), and wherein a pressure sensor (6) determines the gas pressure (7) and the control unit (2) records the pressure and determines a pressure slope (17) and determines a pressure-volume curve (8) from the pressure (7) and the volume (5) and displays it on a display screen (9) or stores it in a retrievable manner. The control unit (2) computes the inspiratory compliance (10) as the quotient of the gas stream and the pressure slope, wherein the inspiratory compliance (10) is preferably displayed on the display screen (9). The control unit (2) computes an LIP (lower inflection point) and/or a UIP (upper inflection point) as a (positive and negative) fraction of, for example, 50-70%, preferably 67% of the maximum inspiratory compliance (14). The control unit (2) uses the LIP (21) and/or the UIP (20) in the pressure-volume curve (8) for the display of a straight line (11), which is defined or delimited by the LIP (21) and the UIP (20). The maximum inspiratory compliance (14) is located, for example, in the middle of the straight line (11).

Figure 2:
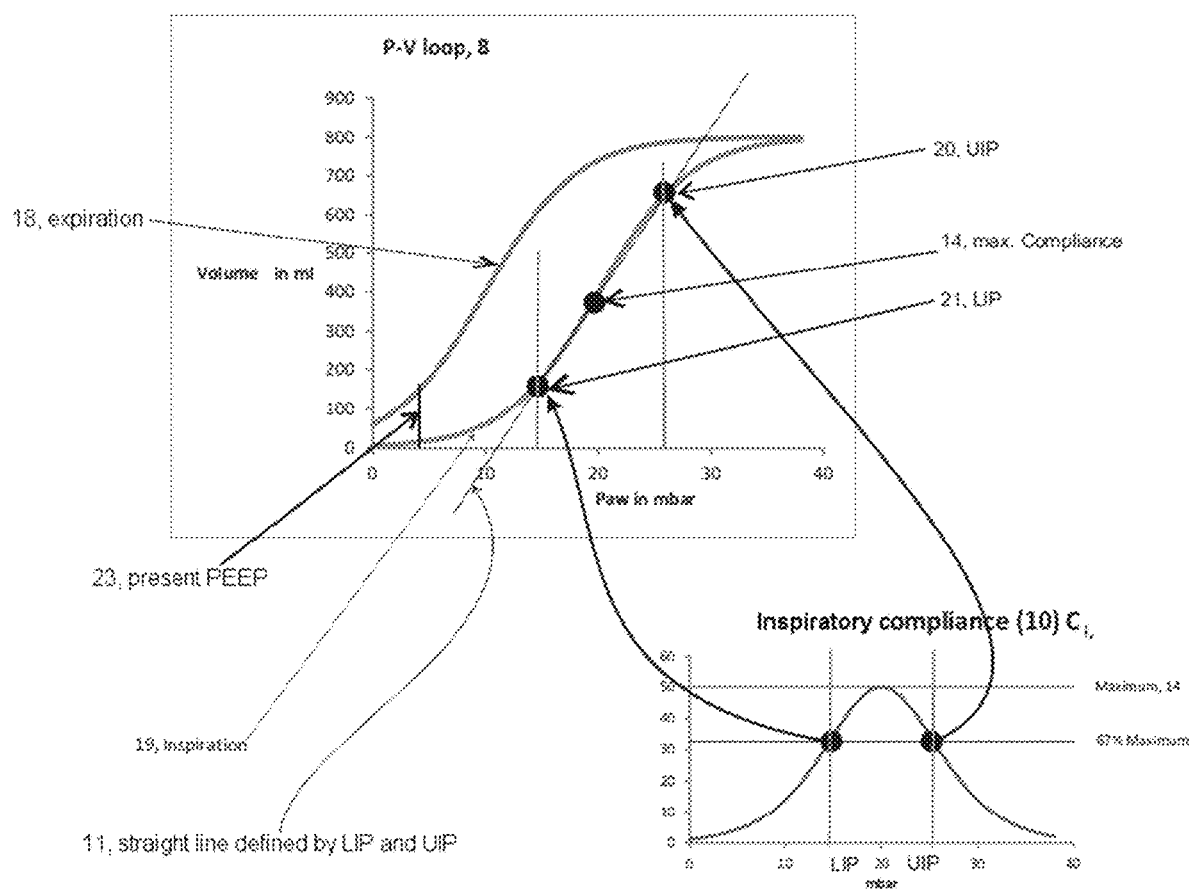
FIG. 2 shows the low flow P-V Tool in the inspiration phase.

FIG. 2 shows the low flow P-V Tool in the inspiration phase.

1. Computation of the pressure slope during the inflation by means of linear regression over 500 measurement points.

The computation only begins, for example, 500 ms after the start of inspiration. The value 500 ms is variable in this case.

The computation is stopped before ending the inflation procedure and the value is kept constant.

$$\frac{dPaw_i}{dt}\bigg|_j = \dot{P}_{i,j} = \frac{500\sum_{j=i}^{i+500} t_j P_{awj} - \sum_{j=i}^{i+500} t_j \sum_{j=i}^{i+500} P_{awj}}{500\sum_{j=i}^{i+500} t_j^2 - \left(\sum_{j=i}^{i+500} t_j\right)^2}$$

2. Computation of the inflationary compliance as a quotient of constant inflationary flow and pressure slope and display of the curve of the inflationary compliance. Determination of the points LIP and UIP as 0.67 Cmax. Numeric display of LIP and UIP $$C_i(t_j) = \frac{\dot{V}_i}{\dot{P}_{i_j}}, \text{ in ml/mbar}$$

$$\dot{V}_i = const.$$

3. Computation of the volume as a summation of the volume stream components $$V(t_j) = 0.001s \sum_{j=0}^{j} \dot{V}_j$$

4. Recording of the pressure-volume curve for the inflation—drawing a straight line through LIP and UIP 5. The straight line through LIP and UIP is to be displaceable according to the invention. If LIP and UIP cannot be determined, a replacement straight line having the slope Cimax is displayed (also displaceable). This straight line is then to go through the point PEEP+(Pmax−PEEP)/2.

Figure 3:
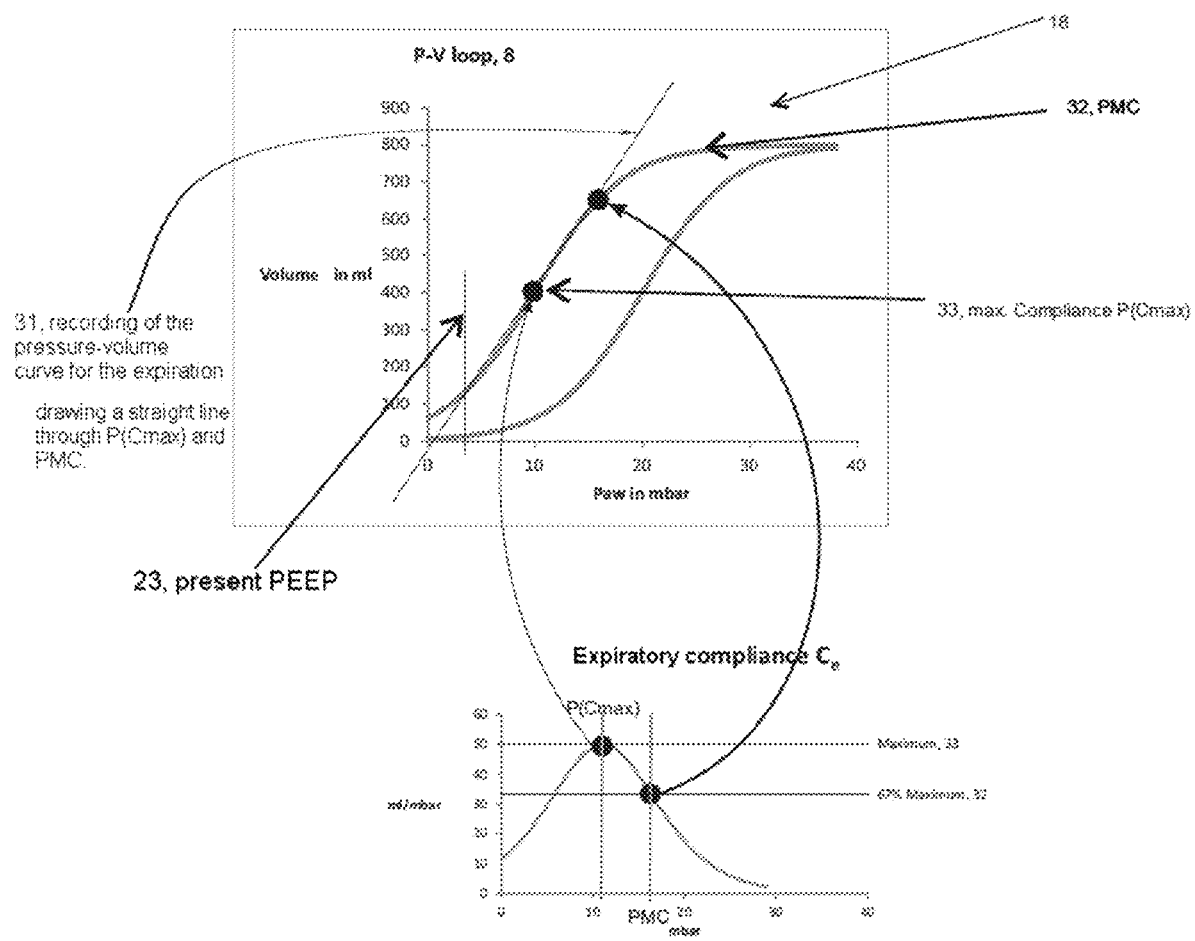
FIG. 3 shows the low flow P-V Tool in the expiration phase.

FIG. 3 shows the low flow P-V Tool in the expiration phase.

The graphic display of C(p) and V(p) is performed with overlay of displaceable lines as shown in the region of the display screen.

1. The computation of the present flow is performed from the sliding mean value (over 0.5 s).

The computation only begins 500 ms after the start of expiration. The end of the computation is 500 ms before the end of expiration. The value 500 ms is variable in this case.

$$\overline{\dot{V}_{e_j}} = \frac{1}{500}\sum_{j=i}^{i+500} \dot{V}_{e_j}$$

2. Computation of the deflationary compliance from quotient of the mean flow and the specified pressure ramp (presently 1 mbar/s). Determination of the points P(Cmax) (33) and PMC (32) at 0.67 Cmax.

The control unit effectuates a numeric display of PMC (32) and/or graphic display of C(p) and V(p) with overlay of displaceable lines on the display screen, (as shown).

$$C_e(t_j) = \frac{\overline{\dot{V}_{e_j}}}{\dot{P}_{def}}, \text{ ml/mbar}$$

$$P_e = const.$$

3. Computation of the volume from summation $$V(t_j) = 0.001s \sum_{j=0}^{j} \dot{V}_j$$

4. Recording of the pressure-volume curve for the expiration—drawing a straight line through P(Cmax) and PMC.

5. The straight line through P(Cmax) and PMC is displaceable.

Figure 4:
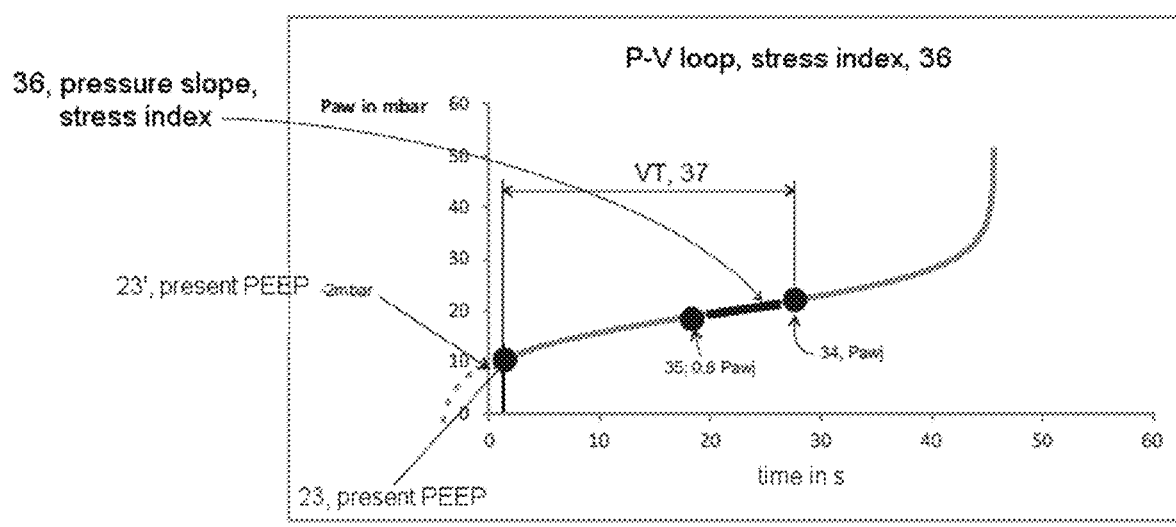
FIG. 4 shows the low flow P-V Tool in the inspiration phase having a curve display and curve analysis of the stress index.

FIG. 4 shows the low flow P-V Tool in the inspiration phase with a curve display and curve analysis of the stress index (36).

1. The breath volume VT (37) is inferred from prior or present respiration and j (38) of VT is computed (at a sampling rate of 1 ms). j is the pressure-volume curve of the studied respiration. The flow is n l/min $$t = \frac{V_T}{\dot{V}} = \frac{V_T}{n}\frac{3}{50}, j|_{V_T} = 1000 V_T \frac{3}{50} = 60 V_T$$

2. Using the present j (38), the pressures Pawj (34) and Pawj80 (35) are determined. Pawj80 (35) is the 80% value or a fraction in the range 65-90% of the pressure Pawj.

It is proposed according to the invention that the PEEP level (23) be selected above the LIP (21) to avoid an end-expiratory collapse of the lung alveoli.

It is proposed according to the invention that the plateau respiration pressure (17) be selected such that the UIP (20) is not exceeded, since the UIP indicates the beginning of the lung distension.

3. The computation of the pressure slope (as in the case of the dynamic compliance) in the range between 0.8 Pawj and Pawj is performed, for example, by means of linear regression.

$$\frac{dPaw_i}{dt}\bigg|_j = \dot{P}_{infj} = \frac{500\sum_{j=i}^{i+500} t_j P_{awj} - \sum_{j=i}^{i+500} t_j \sum_{j=i}^{i+500} P_{awj}}{500\sum_{j=i}^{i+500} t_j^2 - \left(\sum_{j=i}^{i+500} t_j\right)^2}$$

4. Logarithmic expression of the values of time and dp/dt in the range 0.8 Pawj and Pawj and substitution as T and P.

5. Computation of the stress index from the slope of the function P(T) in the range 0.8 Pawj and Pawj $$b_j = \frac{500\sum_{j(0,8P_{awj})}^{j(P_{awj})} T_j P_j - \sum_{j(0,8P_{awj})}^{j(P_{awj})} T_j \sum_{j(0,8P_{awj})}^{j(P_{awj})} P_j}{500\sum_{j(0,8P_{awj})}^{j(P_{awj})} T_j^2 - \left(\sum_{j(0,8P_{awj})}^{j(P_{awj})} T_j\right)^2} + 1$$

The time windows of the pressure-time behavior at constant flow are approximated as a power function according to:

$p = at^b + c$

In this case, the power factor b is significant.
If b<1, there is recruitment,
if b=1, the lung is fully open,
if b>1, the lung is distended.

To carry out a potential regression, the pressure slope is expressed as a logarithm:

$$\ln\left(\frac{dP}{dt}\right) = \ln(ab) + (b-1)\ln(t)$$

if one substitutes ln(dp/dt) with P and ln(t) with T, the following is thus true:

$P = \ln(ab) + (b-1)T$

Now one applies the equation for the slope from the linear regression and obtains b−1 and thus b.

Figure 5:
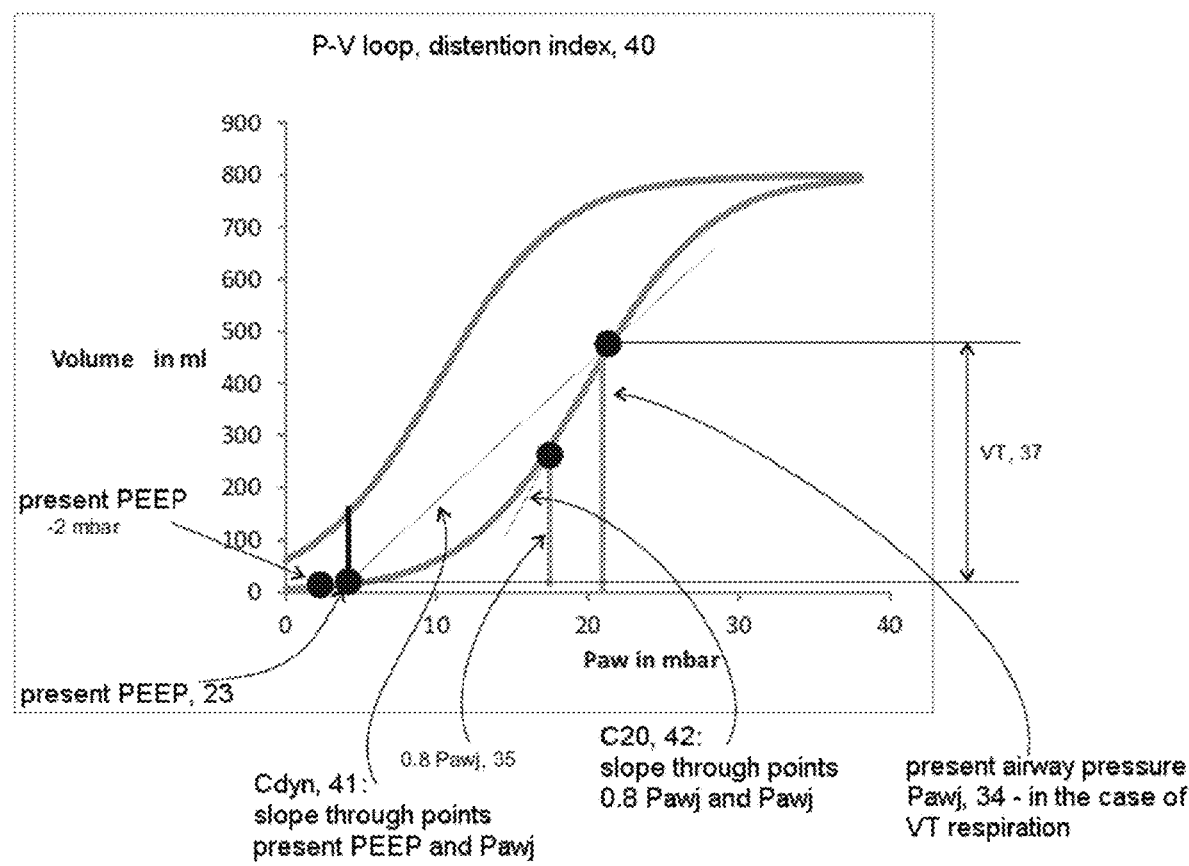
FIG. 5 shows the low flow P-V Tool in the inspiration phase having a curve display and curve analysis of the distention index.

FIG. 5 shows the low flow P-V Tool (8) in the inspiration phase with a curve display and curve analysis of the distention index (40).

1. The control unit computes the distention index (40) C20/Cdyn in the pressure curve (n corresponds to n l/min inspiration flow, i.e. n*50/3 ml/s)

$$\frac{C_{20}}{C_{dyn}} = \frac{\text{slope straight line through } 0.8P_{aw} \text{ and } P_{aw}}{\text{slope straight line through } PEEP \text{ and } P_{aw}}$$

with:

$$C_{20} = \frac{V_j - V_{j80}}{P_{aw_j} - P_{aw_{80}}} = n\frac{50}{3}\frac{t_j - t_{j80}}{P_{aw_j} - P_{aw_{80}}}$$

and $$C_{dyn} = \frac{V_j - V_{PEEP}}{P_{aw_j} - PEEP} = n\frac{50}{3}\frac{t_j}{P_{aw_j} - PEEP}$$

$$\frac{C_{20}}{C_{dyn}} = \frac{t_j - t_{j80}}{P_{aw_j} - P_{aw_{80}}}\frac{P_{aw_j} - PEEP}{t_j} = \left(1 - \frac{t_{j80}}{t_j}\right)\frac{P_{aw_j} - PEEP}{t_j}$$

2. The control unit uses the breath volume VT (37) from the present or the preceding respiration to compute a pressure-volume curve j (38). The present breath volume VT (37) is inferred from prior respiration and j (38) is computed at a sampling rate of 1 ms. The flow is n l/min.

$$t = \frac{V_T}{\dot{V}} = \frac{V_T}{n}\frac{3}{50}; \; j|_{V_T} = 1000V_T\frac{3}{50} = 60V_T$$

3. Using the present j (38), the pressures Pawj (34) and Pawj80 (35) are determined. Pawj80 is the 80% value of the pressure Pawj.

4. The factor or the ratio or a numeric value of the distention index C20/Cdyn (40) of the present breath or breath volume is displayed as a numeric value on the display screen or stored.

5. The distention index C20/Cdyn (40) of the present breath or breath volume is computed as a value from the straight line (41) and the straight line (42), for example from the slopes of the straight lines.

6. The slope through the points present PEEP (23) and Pawj (34) is represented by means of a straight line (41) as Cdyn.

7. The slope through the points 0.8 Pawj (35) and Pawj (34) is represented by means of a straight line (42) as C20.

What is claimed is:

1. A device for recording and displaying a pressure-volume curve, wherein a gas stream is generated by a gas source under control of a control unit and conveyed via a hose to or from a patient, wherein a flow sensor determines the gas stream and the control unit computes and records an administered gas volume, wherein a pressure sensor determines a gas pressure and the control unit records the gas pressure and determines a pressure slope and determines a pressure-volume curve from the gas pressure and the administered gas volume and displays it on a display screen or stores it for a display, and wherein the control unit performs at least one of the following functions (a) to (d):
 (a) computing the pressure-volume curve for inspiration and/or expiration as a function of the gas stream and the pressure slope and computing and displaying steep portions or straight lines of the pressure-volume curve;
 (b) computing a lower inflection point and an upper inflection point and using the lower inflection point and the upper inflection point in the pressure-volume curve for the display of a straight line which is defined or delimited by the lower inflection point and the upper inflection point;
 (c) using a breath volume from a present or prior respiration to compute a pressure-volume curve j and determining pressures Pawj and/or 0.8 Pawj using a value of j;
 (d) recording a pressure-volume curve for an expiration or determining it, wherein the pressure slope is a negative pressure slope and at least one of the gas stream and the administered gas volume may be negative as well.

2. The device of claim 1, wherein at least (a) is performed.

3. The device of claim 1, wherein at least (b) is performed.

4. The device of claim 3, wherein the control unit computes at least one of a lower inflection point and an upper inflection point as 67% of a maximum inspiratory compliance.

5. The device of claim 3, wherein the straight line through lower inflection point and upper inflection point on the display screen is displaceable or changeable by a user selection.

6. The device of claim 3, wherein, if at least one of the lower inflection point and the upper inflection point is not determinable, a replacement straight line having a slope of a maximum inspiratory compliance is displayed.

7. The device of claim 3, wherein a value of at least one of the lower inflection point and the upper inflection point is numerically displayed on the display screen.

8. The device of claim 1, wherein the control unit carries out a computation of the pressure slope by means of linear regression over at least 200 measurement points and the computation only begins 200 ms after start of inspiration or expiration.

9. The device of claim 1, wherein a recording of the pressure-volume curve is started by user selection.

10. The device of claim 1, wherein the control unit executes an automatic analysis of a pressure-volume curve to determine at least one parameter and at least temporarily takes this parameter into consideration for the control of the gas source by the control unit.

11. The device of claim 1, wherein the control unit executes an automatic analysis of a pressure-volume curve to determine at least one parameter and computes a setting value for the control unit for this parameter for the control of the gas source and displays it on the display screen.

12. The device of claim 1, wherein at least (c) is performed.

13. The device of claim 12, wherein the control unit uses a breath volume from a present or prior respiration to compute a pressure-volume curve j.

14. The device of claim 13, wherein the control unit determines at least one of the pressures Pawj and 0.8 Pawj using a value of j.

15. The device of claim 12, wherein the control unit at least one of (i) connects positive end-expiratory pressure and Pawj by means of a straight line as Cdyn and displays it on the display screen (ii) connects 0.8 Pawj and Pawj by means of a straight line as C20 and displays it on the display screen, (iii) determines a pressure slope in a range between 0.8 Pawj and Pawj and displays a corresponding straight line on the display screen, (iv) computes a stress index from a pressure slope between 0.8 Pawj and Pawj and displays it or stores it.

16. The device of claim 1, wherein at least (d) is performed.

17. The device of claim 16, wherein the control unit determines the pressure-volume curve from a quotient of mean flow and specified pressure ramp.

18. The device of claim 16, wherein the control unit determines the points P(Cmax) and PMC from the pressure-volume curve, PMC being a component or fraction of P(Cmax).

19. The device of claim 16, wherein the control unit effectuates at least one of a numeric display of PMC and a graphic display of C(p) and V(p) with overlay of displaceable lines on the display screen.

20. The device of claim 16, wherein the control unit displays the pressure-volume curve for an expiration on the display screen and displays a straight line which intersects the points P(Cmax) and PMC.

* * * * *